United States Patent [19]

Huala et al.

[11] Patent Number: 4,970,147
[45] Date of Patent: Nov. 13, 1990

[54] OXYGEN REGULATABLE GENE EXPRESSION

[75] Inventors: Eva Huala, Belmont; Qing Gu, Cambridge; Lisa Albright, Reading; Frederick Ausubel, Newton, all of Mass.

[73] Assignee: The General Hospital Corporation, Boston, Mass.

[21] Appl. No.: 169,488

[22] Filed: Mar. 17, 1988

[51] Int. Cl.$^5$ .................. C12N 1/21; C12N 15/10; C12N 21/00; C12N 15/67

[52] U.S. Cl. .................. 435/69.1; 435/71.1; 435/91; 435/172.1; 435/172.3; 435/252.3; 435/320; 536/27; 935/6; 935/22; 935/27; 935/8; 935/60; 935/72

[58] Field of Search .................. 435/71.1, 91, 69.1, 435/170, 172.3, 240.2, 252.3, 320; 536/27; 935/10, 24, 6, 33, 61, 66

[56] References Cited

PUBLICATIONS

Ronson et al., 1987, *J. Bacteriol* 169(6):2424–2431.
Birkmann et al., 1987, *MGG* 210: 535–542.
Fischer et al., 1987, *MGG* 209(3):621–626.
Ditta et al., 1987, *J. Bacteriol* 169(7):3217–3223.
Alvarez–Morales et al., 1985, *MGG* 199: 306–314.
Benyon et al., 1988, *EMBO* 7(1): 7–14.
H. M. Fischer et al., EMBO J. 5:1165–1173 (1986).
Conf. Abstract, Proc. 7th Intl. Cong. N≡N Fixation, Mar. 1988.
L. Albright et al., Nitrogen Fixation: Hundred Years After, Proceedings of the 7th International Congress on N=Nitrogen Fixation, Cologne, F.R.G., Mar. 13–20, 1988.
H. Bothe et al., Nitrogen Fixation: Hundred Years After, Proceedings of the 7th International Congress on N=Nitrogen Fixation, Cologne, F.R. G. Mar. 13–20, 1988.
F. J. Bergensen, Nitrogen Fixation: Hundred Years After, Proceedings of the 7th International Congress on N=Nitrogen Fixation, Cologne, F.R.G. Mar. 13–20, 1988.
H. Hennecke et al., Nitrogen Fixation: Hundred Years After, Proceedings of the 7th International Congress on N=Nitrogen Fixation, Cologne, F.R.G. Mar. 13–20, 1988.
B. Thöny et al., Nitrogen Fixation: Hundred Years After Proceedings of the 7th International Congress on N=Nitrogen Fixation, Cologne, F.R.G. Mar. 13–30, 1988.
S. Ebeling et al., Nitrogen Fixation: Hundred Years After, Proceedings of the 7th International Congress on N=Nitrogen Fixation, Cologne, F.R.G. Mar. 13–30, 1988.
M. Gubler et al., Nitrogen Fixation: Hundred Years After, Proceedings of the 7th International Congress on N=Nitrogen Fixation, Cologne, F.R.G. Mar. 13–20, 1988.
M. Göttfert et al., Nitrogen Fixation: Hundred Years After, Proceedings of the 7th International Congress on N=Nitrogen Fixation, Cologne, F.R.G. Mar. 13–20, 1988.

*Primary Examiner*—Richard A. Schwartz
*Assistant Examiner*—Richard Peet
*Attorney, Agent, or Firm*—Saidman, Sterne, Kessler & Goldstein

[57] ABSTRACT

The invention discloses that, in the presence of NifA and NtrA, the expression of a desired DNA molecule which has been operably linked to an ntrA-RNA polymerase and NifA dependent promoter can be regulated by regulating the oxygen level of the culture medium. The invention relates to vectors which may be used in accordance with this discovery, and to methods for using such vectors.

11 Claims, 4 Drawing Sheets

OXYGEN REGULATABLE GENE EXPRESSION

FIELD OF THE INVENTION

The present invention relates to the field of recombinant DNA technology. In particular, the present invention is concerned with a method for controlling gene expression, and with recombinant DNA molecules which may be used in accordance with this method.

BACKGROUND OF THE INVENTION

An ability to control or regulate the expression of a cloned homologous or heterologous gene in a host cell is a central requirement of recombinant DNA technology. Recombinant molecules capable of mediating the expression of such genes and methods for employing such molecules are described by Cohen, et al. (U.S. Pat. Nos. 4,237,224 and 4,468,464).

Although the continual expression of a cloned gene may often be acceptable, it is frequently highly desirable to modulate the expression of a cloned gene. Several methods are currently known for achieving such regulation of gene expression.

One method for regulating gene expression employs plasmid vectors whose copy number can be amplified by increasing the temperature at which the expressing host cell is cultured. Such vectors are described, for example, by Uhlin, et al. (U.S. Pat. Nos. 4,495,287 and 4,499,189).

It is, however frequently more desirable to control gene expression through the use of highly efficient promoter regions which are capable of enabling high level expression of a cloned gene. Such promoter regions may be either constitutive, or, more preferably, regulatable (i.e. promoter regions whose capacity to mediate gene transcription can be regulated by external genes, or culture conditions). Examples of constitutive promoters include the int promoter of bacteriophage λ, the bla promoter of the β-lactamase gene of pBR322, and the CAT promoter of the chloramphenicol acetyl transferase gene of pPR325, etc. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen, I., et al.. *J. Bacteriol.* 162:176–182 (1985)) and the θ-28-specific promoters of *B. subtilis* (Gilman, M.Z., et al., *Gene* 32:11–20 (1984)), the promoters of the bacteriophages of *Bacillus* (Gryczan, T.J., In: *The Molecular Biology of the Bacilli*, Academic Press, Inc., N.Y. (1982)), and *Streotomyces* promoters (Ward, J.M., et al., *Mol. Gen. Genet.* 203:468–478 (1986)). Prokaryotic promoters are reviewed by Glick, B.R., (*J. Ind. Microbiol.* 1:277–282 (1987)); Cenatiempo, Y. (*Biochimie* 68:505–516 (1986)); and Gottesman, S. (*Ann. Rev Genet.* 18:415–442 (1984)).

Examples of eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); and the yeast gal4 gene promoter (Johnston, S.A., et al., *Proc. Natl. Acad. Sci. (USA)* 79:6971–6975 (1982); Silver, Pa., et al., *Proc. Natl. Acad. Sci. (USA)* 81:5951–5955 (1984)).

Although the above-described regulatable promoters are capable of mediating gene expression in response to changes in the conditions at which recipient cells are cultured, such regulation often requires changing the temperature of the culture media, or the introduction of small metabolites or compounds into the culture media. Such requirements are often costly, and, hence unsuitable for the large scale production of a recombinant product. Moreover, such requirement are often inefficient for large scale fermentation and production. Hence, a need exists for a method for regulating gene expression which is amenable to both small and large scale fermentations, and is both economical and efficient.

BRIEF DESCRIPTION OF THE FIGURES

FIG. 4 also shows the results of control experiments involving: a plac plasmid (containing the lacZ gene operably linked to the AphI promoter region); a plasmid containing the lac promoter operably linked to the *K. pneumoniae* nifA gene (pGR397); and a plasmid (pMB210) containing the nifH promoter linked to the lacZ gene without any vector supplying NifA (no driver).

SUMMARY OF THE INVENTION

The invention relates to the discovery that by operably linking a desired DNA molecule to an ntrA-RNA polymerase and NifA dependent promoter it is possible to regulate the expression of the desired DNA molecule by regulating the oxygen level of the culture medium. The invention relates to vectors which may be used in accordance with this discovery, and to methods for using such vectors.

In detail, the invention provides a vector which contains a nifA gene operably linked to a heterologous promoter.

The invention also includes a cell which contains:
  (a) a vector comprising an NtrA-RNA polymerase and NifA dependent promoter; and
  (b) a nifA gene operably linked to a heterologous promoter.

The invention also pertains to a method of regulating the expression of a desired DNA molecule which comprises:
  (a) operably linking the DNA molecule to an NtrA-RNA polymerase and NifA dependent promoter of a vector;
  (b) introducing the vector into a recipient, NtrA expressing host cell;
  (c) providing to the host cell amounts of NifA sufficient to place the transcription from the promoter under oxygen regulation; and
  (d) regulating the expression of the desired DNA molecule by regulating the oxygen level of the culture medium.

DESCRIPTION OF THE PREFERRED EMBODIMENTS

The Regulation of the Expression of the Nitrogen Fixation Genes of Rhizobium Meliloti The *R. meliloti* nifHDKE, nifB, and fixABCX operons are positively regulated by the product of the nifA gene (NifA protein). Expression of the nifA gene is, in turn, regulated, at least in part, by the ambient level of oxygen (Ditta, G., et al., *J. Bact.* 169:3217–3223 (1987), incorporated herein by reference). *R. meliloti* NifA is a structural and functional homologue of analogous proteins in a variety of nitrogen fixing species. The NifA protein has been found to possess three domains: an oxygen-binding amino terminal domain, a central domain which is capable of interacting with NtrA-RNA polymerase, and a carboxy terminal domain.

NtrA is an accessory RNA polymerase sigma factor which is produced by the ntrA gene of *R. meliloti*, and by an analogous ntrA gene in *E. coli*.

The transcription of certain promoters in *R. meliloti* (such as, for example, the *R. meliloti* nifH promoter) has been found to require the presence of both NtrA-RNA polymerase and NifA. Such promoters are hereinafter referred to as "NtrA-RNA polymerase and NifA dependent promoters."

The present invention derives, in part, from the discovery that NifA protein is capable of interacting with NtrA-RNA polymerase and NifA dependent promoters to render the transcription from such promoters sensitive to repression by oxygen. The present invention results, in part, from the discovery that the negative oxygen regulation of the transcription from NtrA-RNA polymerase and NifA dependent promoters is due to the presence of NifA. The NtrA-RNA polymerase and NifA dependent promoters are extremely efficient and powerful. Growth of *R. meliloti* cells under anaerobic conditions strongly activates transcription from these promoters, such that under anaerobic conditions these promoters direct the synthesis of between 1–5% of the protein of an *R. meliloti* cell.

Oxygen Regulatable Gene Expression

As discussed above, transcription from an NtrA-RNA polymerase and NifA dependent promoter of *R. meliloti* is controlled by NtrA, and by the product of the *R. meliloti* nifA gene. One aspect of the present invention derives from the discovery that by operably linking such a promoter region to a DNA molecule having a particular, desired sequence, it is possible to place the transcription and, hence, the expression, of that desired DNA molecule under the oxygen dependant regulation of the nifA gene product. Thus, by providing NifA to a cell which expresses NtrA, one can employ oxygen to regulate the transcription of any DNA molecule which has been operably linked to an NtrA-RNA polymerase and NifA dependent promoter.

As used herein, the term "desired DNA molecule" can be any gene, gene fragment, or oligonucleotide whose transcription or expression is desired. Such molecules may, therefore, include genes which encode enzymes, lymphokines, peptide hormones, immunoglobulin proteins, proteins which confer resistance to plant or animal pathogens, protein factors (such as, for example, TPA, Factor VIII, etc.), and the like. Such molecules may also include fragments of such genes. The desired DNA molecules of the present invention may also include DNA sequences which, when transcribed or translated, are capable of causing the secretion, membrane localization, processing or directed transport of the RNA transcript or protein translation product of any DNA sequence which is co-transcribed or co-translated with the desired DNA molecule. Secretory sequences are disclosed by Casadaban, M., et al. (*Proc. Natl. Acad. Sci. USA.* 76:4530–4533 (1979)), and by Gilbert, W., U.S. Pat. No. 4,411,994).

As used herein, the equivalent terms "expression" or "gene expression" are intended to refer to the transcription of a DNA molecule into RNA, and the translation of such RNA into a polypeptide. The oxygen regulated expression of a desired DNA molecule requires that the DNA molecule be "operably linked" to a DNA molecule which contains the transcriptional regulatory information of an NtrA-RNA polymerase and NifA dependent promoter region. As used herein, the term "promoter" is intended to refer to those regulatory sequences which are sufficient to enable the transcription of an operably linked DNA molecule. The term "promoter region" is intended to refer to those regulatory sequences which are sufficient to enable both the transcription and the translation of an operably linked DNA molecule. An operable linkage is a linkage in which such regulatory DNA sequences and the desired DNA molecule sought to be expressed are connected in such a way as to permit gene expression.

Two DNA molecules (such as a DNA molecule that contains an NtrARNA polymerase and NifA dependent promoter or promoter region sequence and a desired DNA molecule) are said to be operably linked if they are linked together to form a single DNA molecule in which the nature of the linkage does not interfere with the ability of the promoter region to direct the transcription of the desired DNA molecule, or interfere with the ability of the desired DNA molecule to be transcribed by the promoter region. Thus, an NtrA-RNA polymerase and NifA dependent promoter would be operably linked to a DNA molecule if the promoter were capable of transcribing that DNA molecule.

Figure 1:
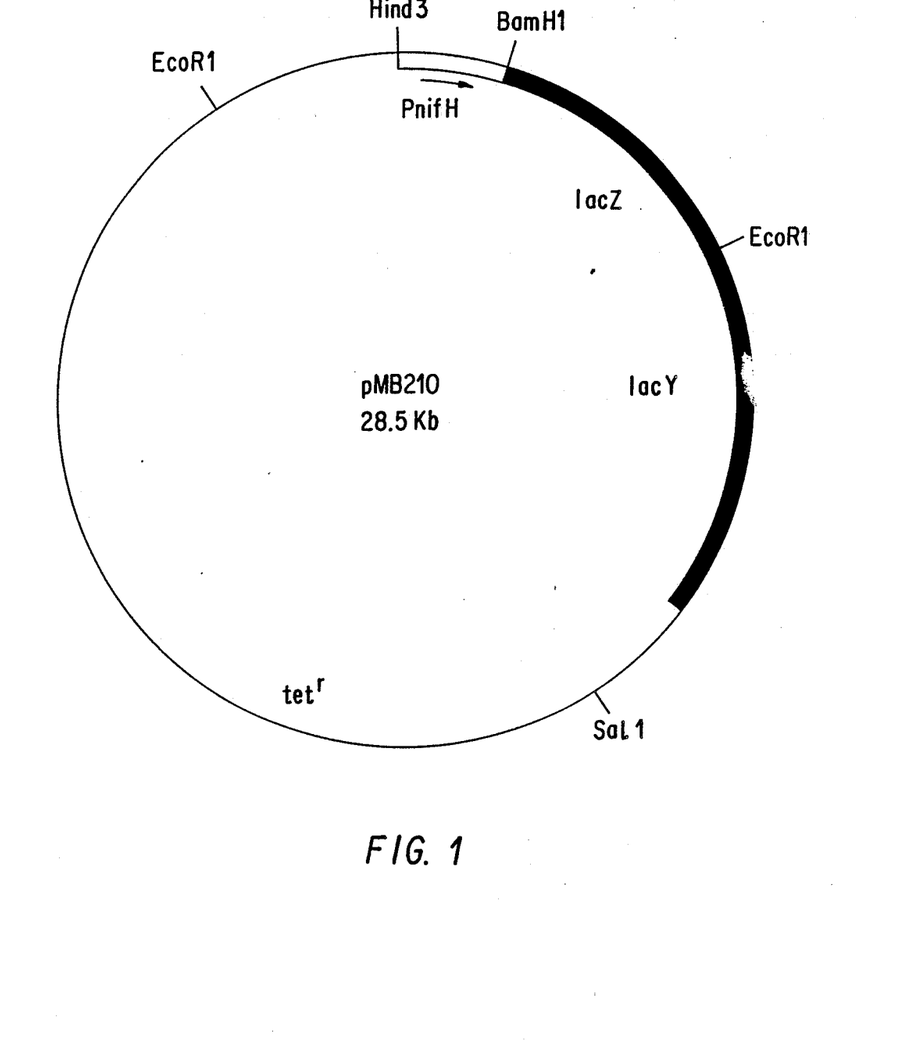
FIG. 1 shows the salient features of plasmid pMB210.

The preferred oxygen regulatable promoter region is the nifH promoter of *R. meliloti*, however, other promoter regions from *R. meliloti*, or from other species of Rhizobium (or other bacteria) provided that transcription from such promoter regions is regulatable in the same manner as the NtrA-RNA polymerase and NifA dependent promoters of the present invention. In addition, one may employ random or site specific mutagenesis techniques in order to obtain mutant promoter regions which display greater or lesser sensitivity to the NifA protein. Such techniques are disclosed, for example, by Miller (*Experiments in Molecular Genetics*, Cold Spring Harbor Press, Cold Spring Harbor, N.Y. (1975)), Kunkel (*Proc. Natl. Acad. Sci. USA*, 82:488–492 (1985)), Nisbet et al. (*Gene Anal. Tech.* 2:23–29 (1985)), and Hines et al. (*Gene* 11:207–218 (1980)). The nifH promoter region of *R. meliloti* is present on plasmid pMB210. The plasmid confers tetracycline resistance to recipient host cells. The salient features of this plasmid are shown in FIG. 1. Plasmid pMB210 contains a translational fusion between the *R. meliloti* nifH promoter and the lacZ gene of *E. coli* (Better, M., et al., *EMBO J.* 4:2419–2424 (1985), herein incorporated by reference). The promoter region of the plasmid can be recovered as a HindIII - BamHI fragment. Alternatively, one or more desired DNA molecules can be operably linked to the *R. meliloti* nifH promoter by introducing such molecules into the BamHI restriction endonuclease recognition site which separates the promoter and the lacZ gene. *E. coli* strain YMC21 (ntrC−/pMB210 was deposited on March 16, 1988 at the American Type Culture Collection, Rockville, Md., U.S.A., and given the designation ATCC 67650.

Figure 2:
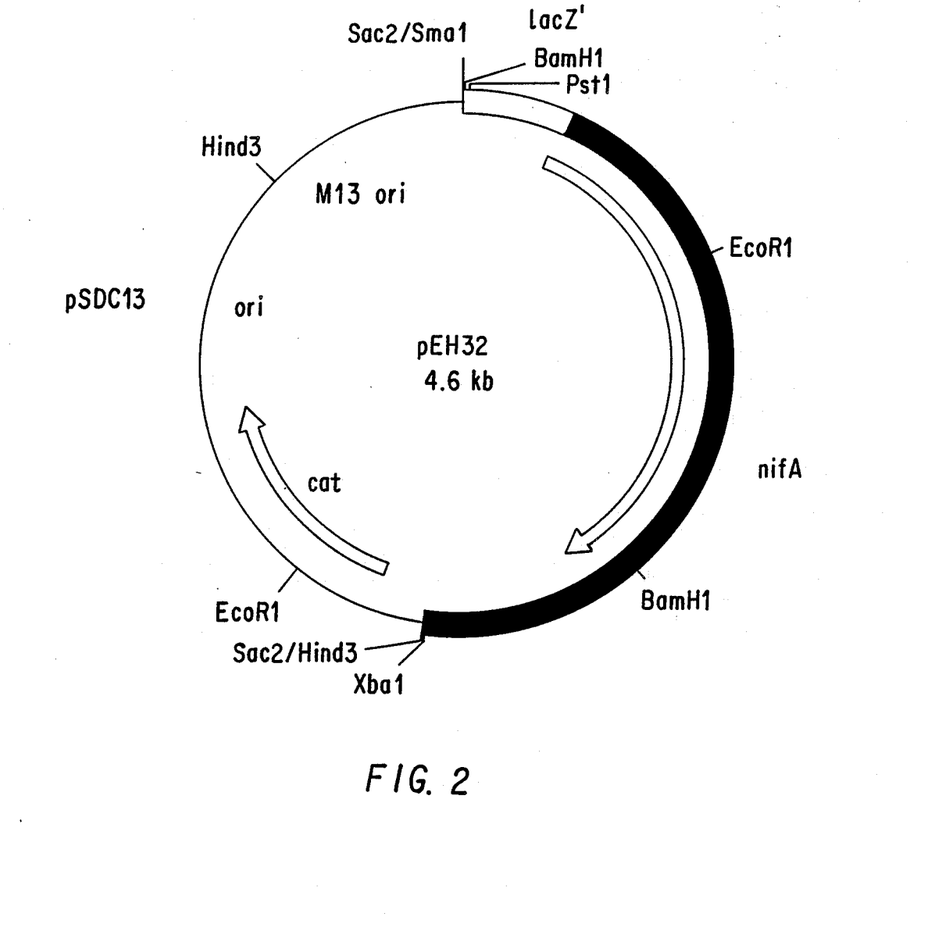
FIG. 2 shows the salient features of plasmid pEH32.

The oxygen regulated expression of the NtrA-RNA polymerase and NifA dependent promoters of the present invention is preferably mediated by the expression of the natural nifA gene of *R. meliloti*, however, other, alternative genes may be employed for this purpose. In addition, one may employ the above-cited techniques of random or site specific mutagenesis in order to obtain mutant NifA genes whose protein products display greater or lesser sensitivity to oxygen. NifA is preferably obtained by the expression of the nifA gene of plasmid pEH32. The esxpression of nifA by this plasmid is directed from a heterologous promoter (i.e. a promoter other than the natural nifA promoter). The plasmid confers chloramphenicol resistance to recipient host cells. The replicons of plasmids pMB210 and pEH32 are compatible, and, thus, both plasmids can be transformed into the same host cell. The salient features of this plasmid are shown in FIG. 2. *E. coli* strain TG1/pEH32 was deposited on March 16, 1988 at the American Type Culture Collection, Rockville, MD, U.S.A., and given the designation ATCC 67651.

The presence of NtrA is also required in order to achieve the oxygen regulated expression of the NtrA-RNA polymerase and NifA dependent promoters of the present invention. This protein is naturally produced in *R. meliloti*, a preferred host cell, and in *E. coli*, the most preferred host cell of the present invention. Thus, in accordance with the present invention it is preferable to employ the endogenous NtrA of such cells. For the purposes of the present invention it is unnecessary to provide additional NtrA to such cells. If, one desires to provide additional NtrA to the cells, it is possible to provide such additional NtrA by providing the cells with a plasmid vector which contains the ntrA gene. Such a vector is described by Ronson, C.W., et al. (*J. Bacteriol.* 169:2424–2431 (1987)), which reference is herein incorporated by reference.

In addition to the presence of an NtrA-RNA polymerase and NifA dependent promoter, a NifA protein and NtrA-RNA polymerase, the oxygen regulated expression of a desired DNA molecule will require the presence of translational control sequences. The precise nature of the translational control regions may vary from organism to organism, but shall in general include DNA molecules which, when transcribed into RNA, will signal the initiation of protein synthesis. Proper expression in a prokaryotic cell requires the presence of a ribosome binding site upstream of the gene-encoding sequence. Such ribosome binding sites are disclosed, for example, by Gold, L., et al. (*Ann. Rev. Microbiol.* 35:365–404 (1981)). For the purposes of the present invention the preferred ribosome binding site is the ribosome binding site of the *R. meliloti* nifH promoter region.

II. Oxygen Regulatable Expression Vectors

The above-described DNA molecules can be introduced into a plasmid in order to form an oxygen regulatable expression vector which is capable of autonomous replication in a host cell. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, pACYC 184, πVX). Such plasmids are, for example, disclosed by Maniatis, T., et al. (In: *Molecular Cloning, A Laboratory Manual*, Cold Spring Harbor Press, Cold Spring Harbor, N.Y. (1982)). *Bacillus* plasmids include pC194, pC221, pT127, etc. Such plasmids are disclosed by Gryczan, T. (In: *The Molecular Biology of the Bacilli*, Academic Press, N.Y. (1982), pp. 307–329). Suitable *Streotomyces* plasmids include pIJ101 (Kendall, K.J., et al., *J. Bacteriol.* 169:4177–4183 (1987)), and streptomyces bacteriophages such as φC31 (Chater, K.F., et al.. In: *Sixth International Symposium on Actinomycetales Biology*, Akademiai Kaido, Budapest, Hungary (1986), pp. 45–54). *Pseudomonas* plasmids are reviewed by John, J.F., et al. (*Rev. Infect. Dis.* 8:693–704 (1986)), and Izaki, K. (*Jpn. J. Bacteriol* 33:729–742 (1978)).

Preferred eukaryotic plasmids include BPV, vaccinia, SV40, 2-micron circle, etc. Such plasmids are well known in the art (Botstein, D., et al., *Miami Wntr. Symp.* 19:265–274 (1982); Broach, J.R., In: *The Molecular Biology of the Yeast Saccharomyces: Life Cycle and Inheritance*, Cold Spring Harbor Laboratory, Cold Spring Harbor, N.Y., p. 445–470 (1981); Broach, J.R., *Cell* 28:203–204 (1982); Bollon, D.P., et al., *J. Clin. Hematol. Oncol.* 10:39–48 (1980); Maniatis, T., In: *Cell Biology: A Comprehensive Treatise*. Vol. 3, *Gene Expression*. Academic Press, N.Y., pp. 563–608 (1980))

The expression vector may be introduced into a recipient host cell by any of several means: transduction, transformation, conjugation, micro-injection, electroporation, etc. It is most preferable to introduce the vector into a cell using transformation.

The properties of the expression vector will depend upon the nature of the operable linkage between the NtrA-RNA polymerase and NifA dependent promoter region and the desired DNA molecule. In one embodiment, the vector contains an NtrA-RNA polymerase and NifA dependent promoter, and, thus, lacks the regulatory sequences required for protein translation. Preferably such a vector will additionally contain restriction endonuclease cleavage sites into which one or more desired DNA molecules can be introduced in order to place their transcription under the control of the NtrA-RNA polymerase and NifA dependent promoter.

In a preferred embodiment, the vector contains an NtrA-RNA polymerase and NifA dependent promoter region, and, thus, contains those sequences required for RNA translation. Preferably, such a vector is specially adapted to contain one or more restriction endonuclease cleavage sites into which one or more desired DNA molecules may be introduced such that the introduction of these desired DNA molecules places their expression under the control of the NtrA-RNA polymerase and NifA dependent promoter and the NifA and NtrA-RNA polymerase proteins. As discussed above, it is possible to incorporate, for example, two desired DNA molecules into the above-described vectors such that the first molecule causes the secretion, transport, etc., of the transcript or translation product of the second molecule.

As discussed above, in addition to endogenous NtrA, the oxygen dependent regulation of transcription of a desired DNA molecule requires that the desired DNA molecule be linked to an NtrA-RNA polymerase and NifA dependent promoter or promoter region, and that NifA be present. In one embodiment, both the nifA gene and the promoter, or promoter region are present on the same plasmid or vector.

Alternatively, however, one may, in accordance with the present invention provide the desired DNA molecule and promoter (or promoter region) and the nifA gene to a cell on two separate plasmids. The use of such a two plasmid expression system has advantages which may be desirable depending upon the nature of the particular desired DNA molecule employed, and the particular host strain in which expression is desired. For example, such a system permits one to introduce the NtrA-RNA polymerase and NifA dependent promoter or promoter region and the nifA gene on plasmid vectors of different stability or copy number.

IV. Application of Oxygen Regulatable Expression Vectors to Gene Expression

The above discussed vectors can be used to place the expression of a desired DNA molecule (which encodes a desired product) under oxygen regulation. In order to accomplish this goal, the desired DNA molecule is inserted into a vector which contains an NtrA-RNA polymerase and NifA dependent promoter region such that it is operably linked to this promoter region. Such an operable linkage can, for example, be obtained by introducing the desired DNA molecule into the BamHI site which separates the R. meliloti nifH promoter and the lacZ gene of plasmid pMB210.

The above-described plasmid containing an NtrA-RNA polymerase and NifA dependent promoter region operably linked to the desired DNA molecule is then introduced (as by transformation) into a host cell (preferably, an E. coli strain) which contains a nifA plasmid (for example, plasmid pEH32).

The transformed cells are then cultured under conditions (i.e. temperature, culture medium, etc) which permit cell growth. In one embodiment, such growth is performed in an atmosphere which contains from about to about 0 to about 5 percent oxygen. Culturing under such conditions results in the de-repression of the R. meliloti nifH promoter, and, therefore, will result in the expression of the desired product.

In a preferred embodiment, the transformed cells are cultured under aerobic conditions (i.e. in an atmosphere of from about 10 to about 21 percent oxygen) until a desired biomass of cells is obtained. Under such conditions, the expression of the desired DNA molecule will be repressed. The culture is then permitted to become anaerobic in order to cause the de-repression of the R. meliloti nifH promoter. Under such anaerobic conditions, expression of the desired DNA molecule occurs. The desired product of this expression can then be recovered using methods well known in the art.

The culture can be made anaerobic by any of a variety of means. For example, oxygen can be removed from the culture through the addition of chemicals or ions which can sequester the oxygen and precipitate it from the culture medium. In a preferred embodiment, the oxygen level of the culture is decreased by simply limiting or terminating the addition of exogenous oxygen to the culture and, thus, permitting the cells to decrease the oxygen level of the culture by respiration. In an alternative preferred embodiment, the culture's oxygen is replaced by providing nitrogen or a similar non-toxic, inert gas to the culture under conditions sufficient to replace the culture's oxygen.

Significantly, it is possible to cycle the culture between aerobic and anaerobic conditions in order to obtain cycles of gene expression and non-expression.

The foregoing will be detailed by the following specific examples which are intended to be merely illustrative of the invention and are not intended to be limited in any way. Variations in the actual processes described in the examples will be apparent to those skilled in the art. Therefore the present invention is not to be considered limited only by the appended claims and not by the following examples.

EXAMPLE 1

A Two-Component Model of Signal Transduction

NifA proteins share homology in the C-terminal and central regions with at least two other transcriptional activators, the NtrC and DctD proteins. Interestingly, NtrC and DctD (but not NifA) also share N-terminal homology for about 120 amino acids with a variety of other proteins including E. coli PhoB, OmpR, SfrA, CheB, CheY, UhpA, and A. tumefaciens VirG. Most of these proteins are transcriptional regulators which belong to two-component regulatory systems. The other component is thought to act as an environmental sensor that sends a signal to the regulatory component. A common feature of all of the sensor components is that about 200 amino acids of the C-terminal region are highly conserved. These regulatory pairs (sensor/regulator) include E. coli NtrB/NtrC (nitrogen limitation), PhoR/PhoB (phosphate limitation), EnvZ/OmpR (altered osmolarity), CpxA/SfrA (presence of F$^-$ cells), CheA/CheY + CheB (chemotaxis signalling and adaptation), R. leguminosarum DctB/DctD (presence of C4-dicarboxylates), A. tumefaciens VirA/VirG (plant exudates) (Nixon, B.T., et al., Proc. Natl. Acad. Sci. (USA) 83:7850–7854 (1986); Ronson, C.W., et al., Cell 49:579–581 (1987); Ronson, C.W., et al., J. Bact. 169:2424–2431 (1987); Ronson, C.W., et al., Nuc. Acids Res. 15:7921–7934 (1987)), R. meliloti FixL/FixJ (oxygen level); E. coli UhpB/UhpA (hexose phosphates).

Based on these observations, a model of signal transduction for the two-component systems has been proposed (Nixon, B.T., et al., Proc. Natl. Acad. Sci. (USA) 83:7850–7854 (1986); Ronson, C.W., et al., Cell 49:579–581 (1987); Ronson, C.W., et al., J. Bact. 169:2424–2431 (1987); Ronson, C.W., et al., Nuc. Acids Res. 15:7921–7934 (1987), which references are herein incorporated by reference). According to the model, the N-terminal domain of the environmental sensor class of proteins perceives an environmental stimulus and transmits a signal to its conserved C-terminal domain through an allosteric alteration. The C-terminal portion of the sensor protein then interacts with and modifies the conserved N-terminal protein of the regulator protein. This modified N-terminal domain is then able to effect the response through an interaction with its central and/or C-terminal domains, the interaction causing a switch in the conformation between inactive and active forms.

A clue to the mechanism by which the N-terminal domain of the regulatory may be activated was provided by the demonstration of Ninfa et al. (*Proc. Acad. Natl. Sci (USA)* 83:5909-5913 (1986)) that NtrB is a protein kinase/phosphatase that activates NtrC by phosphorylation, and inactivates NtrC-phosphate by dephosphorylation. CheA, a member of the sensor class, has recently been shown to autophosphorylate, suggesting that this phosphorylation may be conserved in the two-component systems (Hess, J.F., et al., *Proc. Natl. Acad. Sci. (USA)* 84.7609-7613 (1987)).

EXAMPLE 2

Application of the Two Component Model of Signal Transduction to NifA

The N-terminal domain of NifA is not homologous to the other proteins that comprise the regulator class of proteins in the two-component systems described above. Two observations of the present invention have, however, led to the unexpected finding that NifA may function in a manner analogous to that of the regulatory class of proteins.

First, NifA, NtrC and DctD have been found to share two distinct regions of structural similarity. Each has a helix-turn-helix motif at the very C-terminus. This is a structure characteristic of DNA-binding proteins which bind to a region of dyad symmetry (Drummond, M., et al., *EMBO J.* 5:441-447 (1986)). Correspondingly, NifA-, DctD-, and NtrC-activated promoters contain an upstream sequence of dyad symmetry in the −100 to −150 region which is conserved between promoters sharing the same activator and which may be a DNA binding site for the activator. In most systems, this site is required for maximal expression of the promoter (see below). The consensus NifA upstream activation site is TGTCG-$N_6$-CRACA (Gussin, G.N., *Ann. Rev. Genet.* 20:567-591 (1986)) (R designates purine; A designates pyrimidine).

NifA, NtrC and DctD each work in concert with the alternative sigma factor NtrA (RpoN) to initiate transcription at promoters characterized by the consensus sequence CTGGYAYR-N4-TTGCA, extending approximately from −26 to −10 relative to the transcription start point (Gussin, G.N., *Ann. Rev. Genet.* 20:567-591 (1986)); Ronson, C.W., et al., *Cell* 49:579-581 (1987); Ronson, C.W., et al , *J. Bact.* 169:2424-2431 (1987); Ronson, C.W., et al., *Nuc. Acids Res.* 15:7921-7934 (1987)). The present invention relates, in part, from the discovery that the NtrA protein shares extensive homology in the middle of NifA, NtrC, DctD (Ronson, C.W., et al., *Nuc. Acids Res.* 15:7921-7934 (1987)) and, surprisingly, *E. coli* TyrR, a repressor of aromatic amino acid biosynthesis. This finding suggests that the central domain of NtrA is involved in activation of transcription by RNA core polymerase +NtrA (NtrA-polymerase).

The second reason to think that NifA is analogous to the regulatory proteins in the two component systems derives from the discovery that the NifA proteins of *K. pneumoniae* and *R. meliloti* are post-translationally regulated. In *K. pneumoniae*, NifA-driven transcription is sensitive to oxygen in the presence of NifL (Gussin, G.N., *Ann. Rev. Genet.* 20:567-591 (1986)). By analogy to NtrC and DctD, the N-terminal domain of *K. pneumoniae* NifA might interact with NifL to regulate NifA activity.

These observations led to the discovery that the N-terminal domain of *R. meliloti* NifA confers oxygen sensitivity to the NifA protein.

EXAMPLE 3

Function of the R. Meliloti NifA N-Terminal Domain

As discussed above, a model for the function of two-component regulatory systems groups bacterial proteins involved in transduction of environmental signals into a sensor class and a regulator class. One prediction of this model is that the activity of the regulator class of proteins is modulated through the N-terminal domain. *Rhizobium meliloti* nifA shares homology in its central region with some members of the regulator class of proteins. Although the Nterminal portion of nifA shares no homology with the N-terminal domains of members of the regulator class, this domain may still be involved in modulation of NifA activity.

To investigate the function of *R. meliloti* NifA in free living *Rhizobium*, nifA driver and nifH-lacZ fusion constructions were introduced into a free living *R. meliloti* ntrC− mutant strain. The reason for using the ntrC[31] strain was to prevent NtrC-mediated expression of nifH and fixA promoters in nitrogen starved *R. meliloti* (Szeto, W.W., et al., *J. Bacteriol.* 169:1423-1432 (1987), which reference is herein incorporated by reference). Unexpectedly, there was no induction of the nifH or fixA promoters by *R. meliloti* NifA when the strains were grown in TY or minimal media under normal aerobic conditions. However, if the cultures were placed under microaerobic conditions, both the nifH and fixA promoters were induced.

Figure 3:
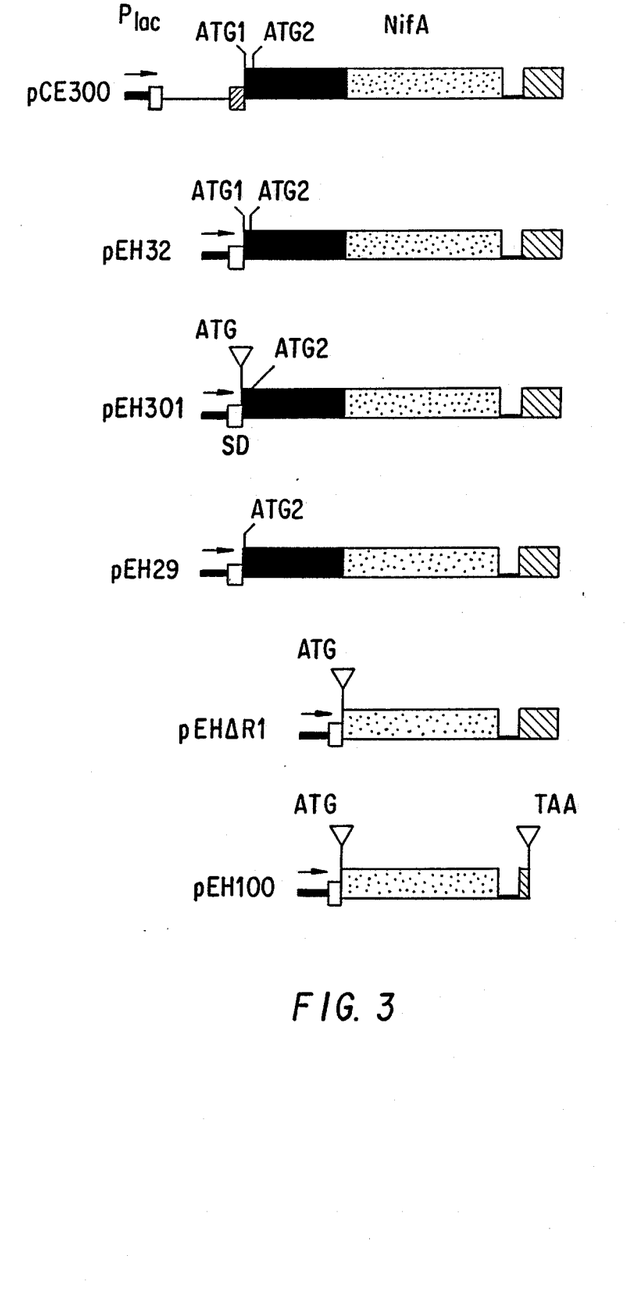
FIG. 3 shows the structures of several nifA constructions. The blackened area represents the sequences of the nifA gene which encode the N-terminal domain of NifA. The dotted area represents the sequences of the nifA gene which encode the central domain of NifA. The large cross-hatched area represents the sequences of the nifA gene which encode the C-terminal domain of NifA. All constructions are transcribed from the lac promoter of *E. coli*. "S D" refers to the Shine-Delgarno sequence; unshaded S D boxes represent the lac S D sequence; cross-hatched boxes represent the nifA S D sequence.
Figure 4:
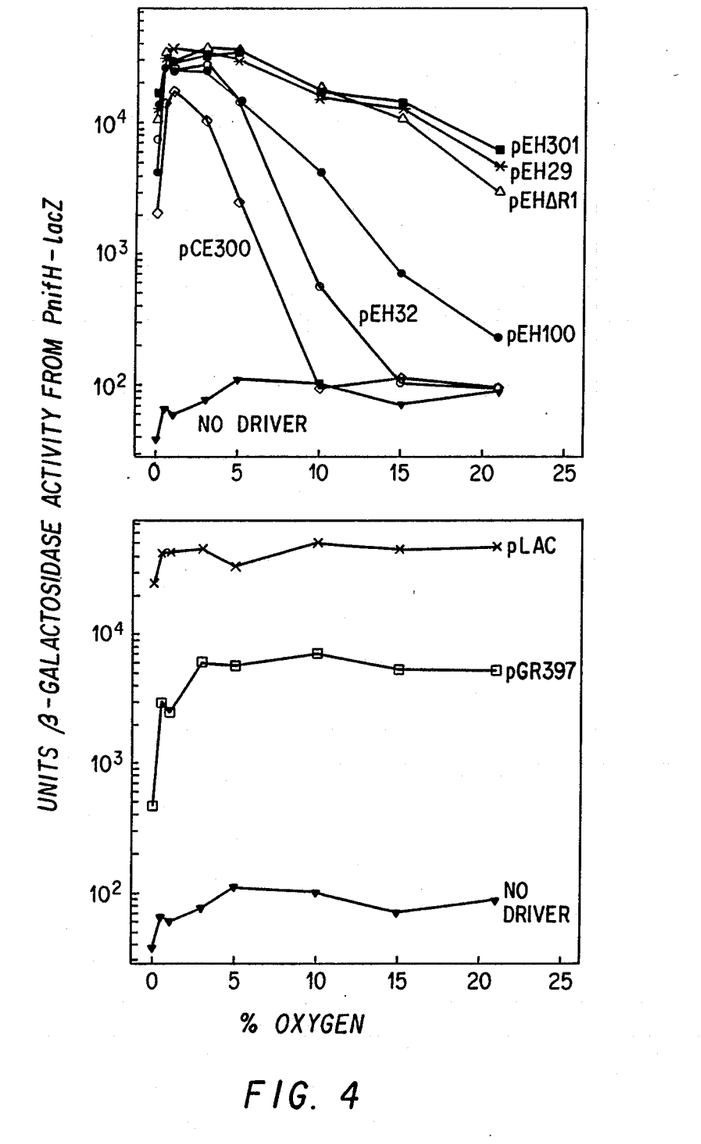
FIG. 4 shows the effect of oxygen on the transcription of the *R. meliloti* nifH promoter.

In order to further characterize the role which the amino terminal domain of *R. meliloti* NifA on activity of the protein, the ability of NifA to drive expression of target lacZ-*R. meliloti* nifH fusions was assayed under various oxygen atmospheres. *E. coli* strain YMC21 (ntrC−) was transformed with plasmid pMB210 which contains an *R. meliloti* nifH-lacZ fusion. The effect of oxygen on the extent and level of transcription of the *R. meliloti* nifH promoter of this fusion can, therefore, be assayed by measuring the amount of beta-galactosidase which is expressed. The cells were then transformed with a second plasmid which contained all or part of the nifA gene (FIG. 3), and cultured in atmospheres having differing percentages of oxygen. The effect of oxygen on the transcription of the *R. meliloti* nifH promoter is shown in FIG. 4. As shown in this Figure, the presence of NifA caused transcription from the *R. meliloti* nifH promoter to become oxygen regulatable. Control experiments show that this sensitivity requires NifA. The NifA protein of *K. pneumoniae* did not cause transcription from the nifH promoter to become sensitive to oxygen. This is due to the absence of the *K. oneumoniae* NifL protein, which is required in combination with *K. oneumoniae* NifA in order to render the transcription sensitive to oxygen regulation. The expression of target *R. meliloti* nifH-lacZ fusions was found to be sensitive to ambient $O_2$ levels in *E. coli*. Similar results were obtained with *R. meliloti*. The results of these experiments are summarized in Table 1. Beynon, J.L., et al. (*EMBO J.* 7:7-14 (1988)) and Fischer, H.-M., et al. (*Molec. Gen. Genet.* 209:621-626 (1986)) have reported that activity of NifA from *R. meliloti* and *B. japonicum*, respectively, appears to be oxygen sensitive.

TABLE 1

O2 Sensitivity of Constitutively Expressed R. Meliloti NifA in R. meliloti and in E. coli

| | | | | Units beta-galactosidase* | | | |
|---|---|---|---|---|---|---|---|
| | | | | +NH$_4^+$ | | −NH$_4^+$ | |
| No. | Host | Driver | Reporter | +O$_2$ | −O$_2$ | +O$_2$ | −O$_2$ |
| 1 | Rm 1021 (WT) | none | none | 5 | 4 | 1 | 4 |
| 2 | Rm 1021 (WT) | none | pMB210 (Rm nifH-lacZ) | 52 ± 18 | 60 ± 23 | 477 ± 150 | 266 ± 160 |
| 3 | Rm 1612 (WT) | none | none | 5 | 4 | 2 | 3 |
| 4 | Rm 1612 (NtrC$^-$) | none | pMB210 (Rm nifH-lacZ) | 38 ± 10 | 36 ± 10 | 26 ± 3 | 24 ± 6 |
| 5 | Rm 1612 (NtrC$^-$) | pSUP107 (vector) | pMB210 (Rm nifH-lacZ) | 51 ± 6 | 56 ± 25 | 44 ± 12 | 43 ± 17 |
| 6 | Rm 1612 (NtrC$^-$) | pQG301 (Rm NifA) | pMB210 (Rm nifH-lacZ) | 51 ± 12 | 500 ± 200 | 48 ± 18 | 322 ± 196 |
| 7 | Rm 1354 (NifA$^-$) | none | none | 4 | 5 | 3 | 5 |
| 8 | Rm 4000 (NifA$^-$) | none | integrated nifH-lacZ | 10 ± 3 | 6 ± 3 | 51 ± 16 | 32 ± 25 |
| 9 | Rm 4000 (NifA$^-$) | pSUP107 (vector) | integrated nifH-lacZ | 10 ± 2 | 10 ± 4 | 40 ± 9 | 31 ± 7 |
| 10 | Rm 4000 (NifA$^-$) | pQG301 (Rm NifA) | integrated nifH-lacZ | 56 ± 32 | 667 ± 205 | 79 ± 40 | 321 ± 120 |
| 11 | Rm 1021 (WT) | none | pMB211 (fixA-lacZ) | 19 | 25 | 263 | 186 |
| 12 | Rm 1612 (NtrC$^-$) | none | pMB211 (fixA-lacZ) | 9 | NT | 6 | 8 |
| 13 | Rm 1612 (NtrC$^-$) | pQG301 (Rm NifA) | pMB211 (fixA-lacZ) | 97 | 409 | NT | NT |
| 14 | Ec YMC21 (NtrC$^-$) | pQG301 (Rm NifA) | pMB210 (nifH-lacZ) | 1130 ± 450 | 2470 ± 730 | 640 ± 340 | 2040 ± 900 |
| 15 | Ec YMC21 (NtrC$^-$) | pEH32 (Rm NifA) | pMB210 (nifH-lacZ) | 380 ± 170 | 1090 ± 340 | 310 ± 200 | 1030 ± 280 |

*Beta-galactosidase units (+/− S.D.) shown above are the mean values from three independent experiments. Data without S.D. are the beta-gal units from one to two experiments. Growth conditions are described in the Materials and Methods. The aerobic or low O$_2$ (anaerobic) condition is indicated as +O$_2$ or −O$_2$. The presence or absence of NH$_3$ is indicated as +NH$_4^+$ or −NH$_4^+$.

The oxygen sensitivity of R. meliloti NifA requires the N-terminal domain: small deletions or insertions at the N-terminus of NifA relieve the O$_2$-sensitivity to a great extent. Deletion of the entire N-terminal domain leaves an active protein with considerably reduced O$_2$-sensitivity.

If the oxygen sensitivity of R. meliloti NifA is mediated by a protein analogous to K. pneumoniae NifL or to the sensor component in the two component systems, then this protein component must be conserved in E. coli. Alternatively, the N-terminal domain of R. meliloti NifA could be sensing O$_2$ or redox potential in a more direct manner, without an intermediary protein. Thus, it is possible that other parts of the NifA protein may be involved in O$_2$ sensitivity, and indeed the protein containing the N-terminal domain deletion does retain some sensitivity to O$_2$.

The above-described experiments provide evidence that nifA is post-transcriptionally regulated, and suggest that microaerobic conditions increase the ability of constitutively expressed R. meliloti nifA to activate the R. meliloti nifH promoter in E. coli. The ability of wild-type NifA to drive expression from the R. meliloti nifH promoter was completely abolished under highly aerobic conditions in E. coli. This post-transcriptional regulation by oxygen represents at least a 1000-fold decrease in NifA activity. Mutant NifA proteins were prepared in which the N-terminal amino acid sequence had been altered. These mutants exhibited greatly reduced oxygen regulation, suggesting a role for the N-terminal domain of NifA in post-transcriptional regulation by oxygen. Experiments carried out in R. meliloti with the same fusions produced similar results.

EXAMPLE 4

Function of the NifA C-Terminal Domain

Although a sequence homologous to the upstream activating sequence in K. pneumoniae nif promoters is present upstream of the R. meliloti nifH promoter, deletion of this site has essentially no effect on expression of the promoter in nodules. Expression of a R. meliloti nifH-lacZ fusion driven by K. pneumoniae NIfA carried on a multicopy plasmid in free-living R. meliloti does not require the upstream binding site, although its presence is required for maximal activity (Better, M., et al., EMBO J. 4:2419-2424 (1985)). Likewise, the expression of a R. meliloti nifH-lacZ fusion in E. coli driven by R. meliloti NifA is also not dependent on the presence of the upstream-binding site; deletion of the upstream site has at most a three-fold effect.

In order to determine the effect of the putative DNA-binding domain at the C-terminus of R. meliloti NifA, a fragment of the NifA protein was prepared which lacked this domain. This construction did, however, contain the N-terminal domain deletion mentioned above and so retains only the core domain and downstream linker region. This molecule was found to still retain a major fraction of the normal NifA activity. Thus, either DNA-binding is retained by the doubly-deleted NifA protein, or DNA-binding is not required for activation of the R. meliloti nifH promoter by R. meliloti NifA.

EXAMPLE 5

Transcriptional Activation by NifA

The deletion studies of R. meliloti NifA protein are consistent with a "DNA-looping" model for transcriptional activation by R. meliloti NifA, which is similar to that of K. pneumoniae NifA (Buck, M., et al., Mol. Microb. 1:243-249 (1987)), E. coli and S. typhimurium NtrC, and yeast GAL4 and GCN4 (Guarente, L., Cell 52:303-305 (1988)). This finding suggests that transcriptional activation involves protein-protein interaction between NtrA-polymerase and NifA. In one extreme of the model, binding of NifA to its upstream site serves only to increase the concentration of NifA in the vicinity of NtrA-polymerase and cognate promoters. The interaction of NifA and NtrA-polymerase would be unaltered by DNA-binding. In the other extreme, binding of NifA to the upstream site could allosterically affect interaction of NifA with NtrA-polymerase.

Studies with E. coli NtrC and K. pneumoniae NifA have shown that the number of helical turns between the upstream binding site and the promoter has a major effect on the ability of these transcriptional activators to function (Buck, M., et al., Mol. Microb. 1:243-249 (1987)). This suggests that DNA-binding and transcriptional activation occur simultaneously. This result is consistent with a category of models in which DNA is an allosteric effector, or, alternatively, it is consistent with models in which the local concentration of NifA is effectively increased only while the protein is bound to DNA, thereby constraining the topology of their interaction.

In the context of the looping model, initiation of transcription at a particular NtrA-RNA polymerase and NifA dependent promoter could be governed by at least three different features of the promoter and its corresponding activator. First, the inherent "strength" of a particular promoter with NtrA-polymerase is most likely mediated by the sequence in the −10 to −26 region. Presumably, proteins such as NifA and NtrC increase a rate-limiting step in transcription initiating at this promoter. The second factor is the ability of the activator to promote transcription through its interaction with NtrA-polymerase, which may be regulated by binding to DNA. A third factor is the affinity of the activator for its binding site upstream of the promoter.

The requirements for an upstream binding site at a particular promoter in vivo might vary depending upon the NtrA-polymerase, the transcriptional activator and the concentration of the activator. In vivo and in vitro experiments with NtrC show that by increasing its concentration one can compensate for deletion of its binding site upstream of the glnAP$_2$ promoter (Austin, S., et al., *Mol. Microb.* 1:92–100 (1987)).

Deletion studies of the *R. meliloti* nifH promoter were performed with NifA produced from a multiple copy plasmid. In both *E. coli* and *R. meliloti*, expression of the nifH promoter driven by chromosomal ntrC depended upon the base promoter sequences at −10 to −26, but was not significantly diminished by deletion of sequences upstream of the base promoter (Table 2). The putative nifA binding site, located at position 31 122, is present in pMB210, pMB1124, and pMB1164. Similarly, expression driven by the nifA driver coding for the 301 translational fusion was not significantly dependent on sequences upstream of the base promoter. Expression driven by the wild type nifA from pEH32 showed about a two-fold decrease upon deletion of the putative UAS. These results indicate that expression of the nifH promoter when driven by high copy number nifA constructions is essentially independent of the conserved upstream site.

By analogy to NtrC, the requirement for an upstream binding site at the *R. meliloti* nifH promoter might be more stringent if NifA were present at lower concentrations.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A vector which contains a nifA gene of *R. meliloti* operably linked to a heterologous promoter, wherein said vector additionally contains an NtrA-RNA polymerase and NifA dependent promoter region of *R. meliloti*.

2. The vector of claim 1 which additionally contains a restriction endonuclease recognition site wherein a desired heterologous DNA molecule when introduced into said site will be operably linked to an NtrA-RNA polymerase and nifA dependent promoter.

3. The vector of claim 2 which additionally contains a desired DNA molecule operably linked to an NtrA-RNA polymerase and NifA dependent promoter.

4. The vector of claim 1 which additionally contains a secretory signal sequence.

5. A cell which contains the vector of claim 1.

6. A cell which contains:
   (a) a vector comprising an NtrA-RNA polymerase and NifA dependent promoter of *R. meliloti*; and
   (b) a nifA gene operably linked to a heterologous promoter.

7. The cell of claim 6 wherein said vector additionally contains a desired DNA molecule operably linked to an NtrA-RNA polymerase and nifA dependent promoter.

8. The cell of claim 6 wherein said nifA gene is present on said vector.

9. A method of regulating the expression of a desired DNA molecule which comprises:
   (a) operably linking said DNA molecule to an NtrA-RNA polymerase and NifA dependent promoter of *R. meliloti* of a vector;
   (b) introducing said vector into a recipient, NtrA expressing host cell;
   (c) providing to said host cell amounts of NifA sufficient to place the transcription from said promoter under oxygen regulation; and
   (d) regulating the expression of said desired DNA molecule by regulating the oxygen level of said culture medium.

TABLE 2

| | | Effect of Upstream Deletions in the nifH Promoter in *E. coli* and *R. meliloti*[1] | | | |
|---|---|---|---|---|---|
| | | Host: | | | |
| | | Ec YMC9 (WT) | RM1021 (WT) | Ec YMC21 (NtrC−) | YM21 |
| | | Driver: | | pQG301 | pEH32 |
| | | none | none | (Rm NifA) | (Rm NifA) |
| | Region | | | Conditions: | |
| Reporter | Deleted[2] | +O$_2$—NH$_4$+ | +O$_2$—NH$_4$ | −O$_2$—NH$_4$ | −O$_2$—NH$_4$ |
| pMB210 | none | 100 (302 ± 117) | 100 (451) | 100 (2260 ± 1030) | 100 (1060 ± 185) |
| pMB1107 | − +37 | 11.5 ± 3.5 | 11 | | 10 |
| pMB1097 | − +10 | 20 ± 6 | 20 | | 13 |
| pMB1156 | − −35 | 105 ± 12 | 178 | 65 ± 42 | 36 ± 4 |
| pMB1246 | − −95 | 148 ± 20 | 152 | 34 ± 9 | 50 ± 13 |
| pMB1124 | − −135 | 111 ± 1 | 109 | 73 ± 28 | 106 ± 32 |
| pMB1164 | − −175 | 79 ± 8 | 106 | 83 ± 51 | 127 ± 53 |

[1]Values are given as a percentage of expression from the wild-type promoter (pMB210). There was considerable variation in absolute beta-galactosidase expression from experiment to experiment; however, the relative expression was quite consistent. Values are the means of 3 independent experiments and are presented with their standard deviation or are the result of a single experiment. Numbers in parentheses are beta-gal units with standard deviation. *E. coli* cells or *R. meliloti* cells were grown as described in the methods. +O$_2$ or −O$_2$ indicates aerobic or microaerobic condition. +NH$_4$+ or −NH$_4$+ indicates the presence or absence of NH$_3$, respectively.
[2]The numbers indicate the start site of nifH deletion promoters with respect of the transcription start site of the wild-type nifH promoter (Better, M., et al., EMBO J. 4:2419–2424 (1985)).

10. The method of claim 9 wherein said vector contains a nifA gene.

11. The method of claim 9 wherein said vector additionally contains a secretory signal sequence.

* * * * *